United States Patent
Yoshino

(10) Patent No.: US 9,451,876 B2
(45) Date of Patent: Sep. 27, 2016

(54) ENDOSCOPE SYSTEM AND FOCUS CONTROL METHOD FOR ENDOSCOPE SYSTEM

(71) Applicant: OLYMPUS CORPORATION, Tokyo (JP)

(72) Inventor: Koichiro Yoshino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 389 days.

(21) Appl. No.: 14/058,655

(22) Filed: Oct. 21, 2013

(65) Prior Publication Data
US 2015/0112128 A1 Apr. 23, 2015

(51) Int. Cl.
A61B 1/04 (2006.01)
A61B 1/06 (2006.01)
H04N 7/18 (2006.01)
H04N 5/232 (2006.01)
G03B 17/00 (2006.01)
A61B 1/00 (2006.01)

(52) U.S. Cl.
CPC ....... *A61B 1/00188* (2013.01); *A61B 1/00009* (2013.01); *A61B 1/043* (2013.01); *A61B 1/0638* (2013.01)

(58) Field of Classification Search
CPC . A61B 1/00188; A61B 1/043; A61B 1/0638
USPC .......... 600/103, 118, 167, 172–173
See application file for complete search history.

(56) References Cited

U.S. PATENT DOCUMENTS

| 5,325,146 A * | 6/1994 | Toji ................. G02B 7/102 348/353 |
| 8,444,548 B2 * | 5/2013 | Kumei ............... A61B 1/018 348/65 |
| 8,836,776 B2 * | 9/2014 | Konno ............... A61B 1/04 348/46 |

(Continued)

FOREIGN PATENT DOCUMENTS

| JP | 2011-139760 A | 7/2011 |
| JP | 2013230289 A | 11/2013 |
| WO | 2012/029357 A1 | 3/2012 |

OTHER PUBLICATIONS

Japanese Office Action dated Feb. 2, 2016 from related Japanese Patent Application No. 2012-104472, together with an English language translation.

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

An endoscope system includes an in-focus object plane position switch section that switches an in-focus object plane position of an imaging section, a target in-focus position determination section that calculates an in-focus evaluation value, and determines a target in-focus position based on the in-focus evaluation value, and a change-in-scene detection section that detects whether or not a change in scene has occurred based on a captured image. The target in-focus position determination section determines whether or not the in-focus evaluation value satisfies a determination criterion until the change-in-scene detection section detects that the change in scene has occurred, and selects the first in-focus object plane position or the second in-focus object plane position that is not currently selected by the in-focus object plane position switch section when it has been determined that the in-focus evaluation value does not satisfy the determination criterion.

20 Claims, 9 Drawing Sheets

(56) References Cited

U.S. PATENT DOCUMENTS

| | | | |
|---|---|---|---|
| 2004/0257438 A1* | 12/2004 | Doguchi | A61B 1/00009 348/65 |
| 2007/0055104 A1* | 3/2007 | Kumei | A61B 1/018 600/176 |
| 2008/0021271 A1* | 1/2008 | Pasero | A61B 1/00039 600/109 |
| 2013/0038708 A1 | 2/2013 | Iwasaki | |
| 2013/0217965 A1* | 8/2013 | Sasamoto | G02B 7/08 600/109 |
| 2015/0080651 A1* | 3/2015 | Azuma | A61B 1/06 600/103 |

* cited by examiner

FIG. 4A

| CHANGE IN SCENE | SELECTED IN-FOCUS OBJECT PLANE POSITION | IN-FOCUS EVALUATION VALUE TO BE ACQUIRED | IN-FOCUS DETERMINATION | DETERMINATION RESULT | TARGET IN-FOCUS POSITION |
|---|---|---|---|---|---|
| NO | NEAR | Val_Near | Val_Near > Th_Focus | IN-FOCUS STATE | NEAR |
| | | | Val_Near < Th_Focus | DEFOCUSED STATE | FAR |
| | FAR | Val_Far | Val_Far > Th_Focus | IN-FOCUS STATE | FAR |
| | | | Val_Far < Th_Focus | DEFOCUSED STATE | NEAR |

FIG. 4B

| CHANGE IN SCENE | SELECTED IN-FOCUS OBJECT PLANE POSITION | IN-FOCUS EVALUATION VALUE TO BE ACQUIRED | IN-FOCUS EVALUATION VALUE COMPARISON | TARGET IN-FOCUS POSITION | THRESHOLD VALUE UPDATE |
|---|---|---|---|---|---|
| YES | NEAR | Val_Near, Val_Far | Val_Near > Val_Far | NEAR | Th_Focus_New → Th_Focus |
| | | | Val_Near < Val_Far | FAR | |
| | FAR | Val_Near, Val_Far | Val_Near > Val_Far | NEAR | |
| | | | Val_Near < Val_Far | FAR | |

ENDOSCOPE SYSTEM AND FOCUS CONTROL METHOD FOR ENDOSCOPE SYSTEM

BACKGROUND

The present invention relates to an endoscope system, a focus control method for an endoscope system, and the like.

An endoscope system used for screening examination is required to achieve as deep a depth of field as possible since the user observes a deep digestive tract. In recent years, the number of pixels of the image sensor used for the endoscope system has been increased, and it has become difficult to capture a panfocus (deep-focus) image since the aperture is limited due to the diffraction limit. Since the user must perform a manual focus adjustment or the like when it is difficult to capture a panfocus (deep-focus) image, the operation becomes complex.

For example, JP-A-2011-139760 discloses an endoscope system that reduces complexity due to manual focus control to improve operability by implementing an autofocus (AF) control process that utilizes an area division method and a contrast method.

SUMMARY

According to one aspect of the invention, there is provided an endoscope system comprising:

an in-focus object plane position switch section that selects a first in-focus object plane position or a second in-focus object plane position to switch an in-focus object plane position of an imaging section to the first in-focus object plane position or the second in-focus object plane position;

a target in-focus position determination section that calculates an in-focus evaluation value based on a captured image acquired by the imaging section, and determines a target in-focus position based on the in-focus evaluation value, the target in-focus position being the in-focus object plane position to which the in-focus object plane position of the imaging section is switched by the in-focus object plane position switch section; and a change-in-scene detection section that detects whether or not a change in scene has occurred based on the captured image, the target in-focus position determination section determining whether or not the in-focus evaluation value satisfies a determination criterion until the change-in-scene detection section detects that the change in scene has occurred, and selecting the first in-focus object plane position or the second in-focus object plane position that is not currently selected by the in-focus object plane position switch section to be the target in-focus position when the target in-focus position determination section has determined that the in-focus evaluation value does not satisfy the determination criterion.

According to another aspect of the invention, there is provided a focus control method for an endoscope system comprising:

calculating an in-focus evaluation value based on a captured image acquired by an imaging section;

detecting whether or not a change in scene has occurred based on the captured image;

determining whether or not the in-focus evaluation value satisfies a determination criterion until it is detected that the change in scene has occurred;

determining a first in-focus object plane position or a second in-focus object plane position that is not currently selected to be a target in-focus position when it has been determined that the in-focus evaluation value does not satisfy the determination criterion, the first in-focus object plane position or the second in-focus object plane position being set to an in-focus object plane position of the imaging section; and switching the in-focus object plane position of the imaging section to the target in-focus position.

BRIEF DESCRIPTION OF THE DRAWINGS

FIGS. 4A and 4B are views illustrating the operation of a target in-focus position determination section.

DESCRIPTION OF EXEMPLARY EMBODIMENTS

Figure 1:
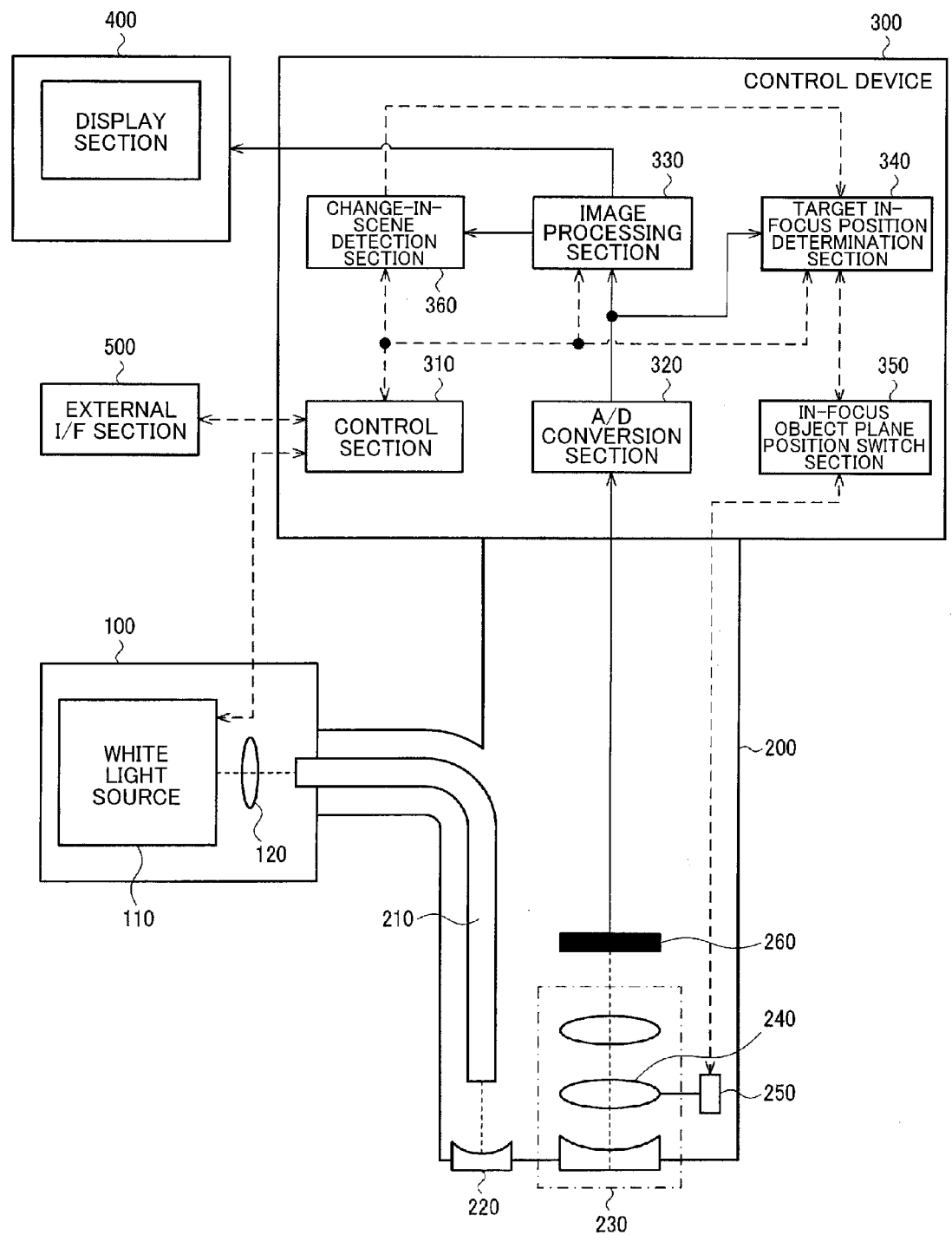
FIG. 1 illustrates a configuration example of an endoscope system according to a first embodiment.

According to one embodiment of the invention, there is provided an endoscope system comprising:

an in-focus object plane position switch section that selects a first in-focus object plane position or a second in-focus object plane position to switch an in-focus object plane position of an imaging section to the first in-focus object plane position or the second in-focus object plane position;

a target in-focus position determination section that calculates an in-focus evaluation value based on a captured image acquired by the imaging section, and determines a target in-focus position based on the in-focus evaluation value, the target in-focus position being the in-focus object plane position to which the in-focus object plane position of the imaging section is switched by the in-focus object plane position switch section; and a change-in-scene detection section that detects whether or not a change in scene has occurred based on the captured image, the target in-focus position determination section determining whether or not the in-focus evaluation value satisfies a determination criterion until the change-in-scene detection section detects that the change in scene has occurred, and selecting the first in-focus object plane position or the second in-focus object plane position that is not currently selected by the in-focus object plane position switch section to be the target in-focus position when the target in-focus position determination section has determined that the in-focus evaluation value does not satisfy the determination criterion.

According to one aspect of the invention, the in-focus object plane position of the imaging section is switched to the first in-focus object plane position or the second in-focus object plane position based on the in-focus evaluation value. In this case, the in-focus object plane position of the imaging section is switched to the first in-focus object plane position or the second in-focus object plane position that is not currently selected when it has been determined that the in-focus evaluation value does not satisfy the determination criterion. This makes it possible to reduce the in-focus object plane position switch frequency.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Outline

An outline of the embodiments of the invention is described below. Note that the in-focus position of the object is hereinafter referred to as "in-focus object plane position". Specifically, the term "in-focus object plane position" refers to the position of the object plane that corresponds to the image plane formed through the focus lens when the image plane formed through the focus lens coincides with the imaging plane of the image sensor.

A panfocus (deep-focus) image is required for screening examination that utilizes an endoscope system. In recent years, it has become difficult to obtain a panfocus (deep-focus) image along with an increase in the number of pixels of the image sensor in order to observe a deep digestive tract. An endoscope system that performs an AF control process may be used to compensate for a decrease in depth of field.

It is desirable that an endoscope system such as an endoscope system that performs an AF control process have a deep depth of field so that the user can simultaneously observe the object over a wide range. When performing screening examination, the observation target area for the user repeatedly undergoes an in-focus state and a defocused state if the in-focus object plane position of the endoscope system frequently and finely changes due to the AF control process. This may increase the burden imposed on the user (e.g., the user may have to continuously observe an identical area for a long time). Therefore, an AF control process that can minimize a change in in-focus object plane position is desired for the endoscope system.

Figure 2:
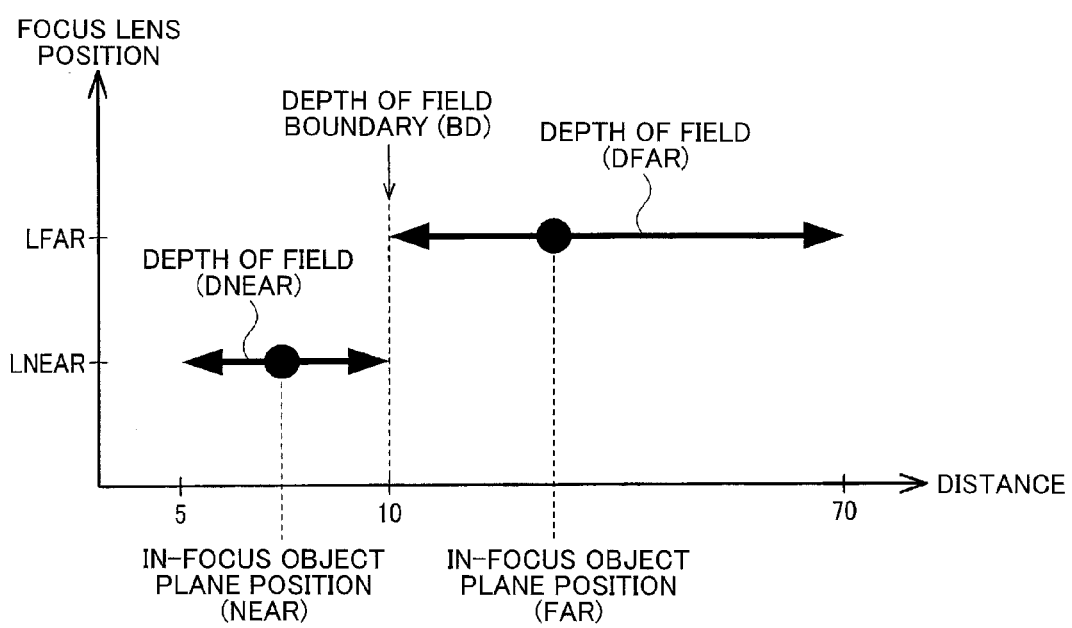
FIG. 2 is a view illustrating an in-focus object plane position and a depth of field.

According to the embodiments of the invention, an endoscope system is configured so that it is possible to select one of an in-focus object plane position NEAR and an in-focus object plane position FAR that are set in advance (see FIG. 2 and the like). The endoscope system is configured so that the depth of field (e.g., about 5 to about 70 mm) required for screening examination can be completely covered by a depth of field DNEAR (e.g., about 5 to about 10 mm) when the in-focus object plane position NEAR is selected, and a depth of field DFAR (e.g., about 10 to about 70 mm) when the in-focus object plane position FAR is selected.

This makes it possible to bring the observation target area for the user into focus by merely performing an AF control process that selects the in-focus object plane position NEAR or the in-focus object plane position FAR. An image in which the object is in focus over a wide range can be acquired corresponding to the in-focus object plane position NEAR or the in-focus object plane position FAR as a result of implementing such an endoscope system. Since it suffices for the AF control process to merely select one of the two in-focus object plane positions, it is possible to reduce the in-focus object plane position switch frequency, and reduce the burden imposed on the user during screening examination as compared with a known contrast AF control process or the like that allows selection of a large number of in-focus object plane positions.

However, the AF control process may pose a problem when determining the in-focus object plane position even when implementing such an endoscope system. For example, a contrast AF control method may be employed that sequentially selects the in-focus object plane position NEAR and the in-focus object plane position FAR, calculates the contrast value from the image acquired corresponding to each in-focus object plane position, and changes the in-focus object plane position of the endoscope system to the in-focus object plane position NEAR or the in-focus object plane position FAR at which a larger contrast value is obtained. According to this method, it is necessary to continuously perform the AF control process that sequentially selects the in-focus object plane position NEAR and the in-focus object plane position FAR at an arbitrary timing. Therefore, since an in-focus state and a defocused state repeatedly occur when the AF control process is performed, the burden imposed on the user may increase (e.g., the user may have to continuously observe an identical area for a long time).

According to the embodiments of the invention, whether or not the object is in focus is determined using a captured image (image signal) at the in-focus object plane position that is selected during observation. The currently selected in-focus object plane position is maintained when it has been determined that the captured image (object) is in focus, and the in-focus object plane position that differs from the currently selected in-focus object plane position is selected when it has been determined that the captured image (object) is out of focus.

According to the above configuration, since the AF control process can be performed without sequentially selecting the in-focus object plane position NEAR and the in-focus object plane position FAR, an in-focus state and a defocused state do not repeatedly occur, and the user can always observe an in-focus image.

The contrast of the image acquired by the endoscope system differs (changes) to a large extent depending on the object. For example, the object observed using the endoscope system may have only small number of high-contrast surface structures (e.g., blood vessels), or may have a large number of high-contrast structures (e.g., blood vessels and protruding mucous membranes). Therefore, the contrast of the image acquired by the endoscope system differs (changes) to a large extent depending on the object.

The contrast of the image acquired by the endoscope system also changes to a large extent depending on the operation (e.g., discharge operation, suction operation, or procedure operation) performed on the object. For example, the user of the endoscope system may improve the visibility of the structure of a digestive tract by spraying a pigment to the digestive tract (i.e., object). In this case, since the contrast of the structure of the object changes to a large extent, the contrast of the image acquired by the endoscope system also changes to a large extent.

The contrast of the image acquired by the endoscope system also differs (changes) to a large extent depending on the imaging condition (e.g., observation mode or image processing). For example, the contrast of the image acquired by the endoscope system differs to a large extent between normal light observation and special light observation (e.g., narrow band imaging (NBI)) even when an identical object is observed. The contrast of the image acquired by the endoscope system also differs (changes) depending on the difference in enhancement process that enhances the contrast of the image, or the difference in noise reduction process.

An image that has a high contrast may be acquired even if the object is out of focus, or an image that has a low contrast may be acquired even if the object is in focus, due to a change in contrast of the image. Therefore, it is very difficult to accurately determine whether or not the object is in focus using the captured image that corresponds to a single in-focus object plane position.

According to the embodiments of the invention, it is determined that the object is in focus when the contrast value is larger than a threshold value, and it is determined that the object is out of focus when the contrast value is smaller than the threshold value. A change in object, a change in operation performed on the object, or a change in imaging condition is detected as a change in scene, and the determination threshold value is updated corresponding to the contrast value of a new scene when a change in scene has been detected.

It is possible to accurately determine whether or not the object is in focus based on the captured image that corresponds to the selected in-focus object plane position by thus updating the threshold value corresponding to the scene. This makes it possible to implement an AF control process that minimizes a situation in which the observation target area for the user is out of focus, and is stable even if a change in contrast of the object or a change in imaging condition of the endoscope system has occurred, and reduce the burden imposed on the user during screening examination.

2. First Embodiment 2.1. Endoscope system

A first embodiment of the invention is described in detail below. FIG. 1 illustrates a configuration example of an endoscope system according to the first embodiment. The endoscope system illustrated in FIG. 1 includes a light source section 100, an imaging section 200, a control device 300 (processing section), a display section 400, and an external I/F section 500.

The light source section 100 includes a white light source 110 that emits white light, and a condenser lens 120 that focuses the white light on a light guide fiber 210.

The imaging section 200 is formed to be elongated and flexible so that the imaging section 200 can be inserted into a body cavity or the like. The imaging section 200 includes the light guide fiber 210 that guides the light focused by the light source section 100, an illumination lens 220 that diffuses the light guided by the light guide fiber 210 to illuminate the observation target, and an objective lens system 230 that receives reflected light from the observation target to form an image. The objective lens system 230 includes a focus lens 240 that adjusts the in-focus object plane position. The imaging section 200 also includes a focus lens driver section 250 that drives the focus lens 240, and an image sensor 260 subjects the reflected light to photoelectric conversion to acquire image signals.

The focus lens driver section 250 is implemented by a voice coil motor (VCM), for example. The image sensor 260 includes a Bayer color filter array, for example. The image sensor 260 sequentially outputs the acquired image signals to an A/D conversion section 320 included in the control device 300 at given time intervals.

The control device 300 includes a control section 310, the A/D conversion section 320, an image processing section 330, a target in-focus position determination section 340 (target in-focus position control section), an in-focus object plane position switch section 350 (switch control section), and a change-in-scene detection section 360.

The A/D conversion section 320 converts the analog image signals sequentially output from the image sensor 260 into digital image signals, and sequentially outputs the digital image signals to the image processing section 330 and the target in-focus position determination section 340.

The image processing section 330 performs image processing (e.g., white balance process, interpolation process (demosaicing process), color conversion process, grayscale transformation process, contrast enhancement process, and noise reduction process) on the image signals output from the AD conversion section 320, and outputs the resulting image signals to the change-in-scene detection section 360 and the display section 400. The display section 400 is implemented by a liquid crystal monitor or the like, and sequentially displays the image signals output from the image processing section 330.

The control section 310 is connected to the external I/F section 500, the white light source 110, the image processing section 330, the target in-focus position determination section 340, and the change-in-scene detection section 360, and controls the external I/F section 500, the white light source 110, the image processing section 330, the target in-focus position determination section 340, and the change-in-scene detection section 360 based on input information from the external I/F section 500. The external I/F section 500 is an interface that allows the user to input information to the endoscope system, for example. For example, the external I/F section 500 includes a start button (imaging start/stop button), an AF start/stop button, an adjustment button for adjusting the imaging condition or the image processing parameter, and the like.

The change-in-scene detection section 360 detects a change in scene based on the image signals output from the image processing section 330, and outputs change-in-scene information (information that indicates the presence or absence of a change in scene) to the target in-focus position determination section 340. The details of the change-in-scene detection section 360 are described later.

The target in-focus position determination section 340 determines a target in-focus position based on the image signals output from the A/D conversion section 320 and the change-in-scene information output from the change-in-scene detection section 360, and outputs target in-focus position information to the in-focus object plane position switch section 350. Note that the term "target in-focus position" used herein refers to the target in-focus object plane position that is either the in-focus object plane position NEAR or the in-focus object plane position FAR. Specifically, the term "target in-focus position" used herein refers to the target in-focus object plane position of the target in-focus position switch control process performed by the in-focus object plane position switch section 350. The details of the target in-focus position determination section 340 are described later.

The in-focus object plane position switch section 350 is connected to the focus lens driver section 250 and the target in-focus position determination section 340. The in-focus object plane position switch section 350 switches the in-focus object plane position of the endoscope system by adjusting the position of the focus lens 240 based on the target in-focus position information output from the target in-focus position determination section 340.

2.2. In-Focus Object Plane Position Switch Section

The relationship between the operation of the in-focus object plane position switch section 350 and the depth of field is described in detail below. As illustrated in FIG. 2, the in-focus object plane position switch section 350 selects the in-focus object plane position NEAR or the in-focus object plane position FAR based on the target in-focus position information output from the target in-focus position determination section 340 so that the depth of field of the endoscope system is set to either the depth of field DNEAR or the depth of field DFAR, and switches the in-focus object plane position of the endoscope system to the selected in-focus object plane position.

The target in-focus position information output from the target in-focus position determination section 340 indicates whether to select the in-focus object plane position NEAR or the in-focus object plane position FAR. The in-focus object plane position NEAR and the in-focus object plane position FAR for implementing the depth of field DNEAR and the depth of field DFAR, a focus lens position LNEAR and a focus lens position LFAR that correspond to the in-focus object plane position NEAR and the in-focus object plane position FAR (see FIG. 2) can be calculated from the design data of the objective lens system 230. Therefore, the in-focus object plane position switch section 350 can switch the in-focus object plane position of the endoscope system to the in-focus object plane position NEAR or the in-focus object plane position FAR, and switch the depth of field of the endoscope system to the depth of field DNEAR or the depth of field DFAR by adjusting the position of the focus lens to the focus lens position LNEAR or the focus lens position LFAR by controlling the focus lens driver section 250.

Note that the term "in-focus object plane position" used herein refers to the position of the object that is in focus. For example, the in-focus object plane position is indicated by the distance from the end of the imaging section to the object. The contrast value becomes a maximum at the in-focus object plane position within the depth of field, for example. Since the object is considered to be in focus as long as the object lies within the depth of field, the in-focus object plane position may be set to an arbitrary position within the depth of field. When the in-focus object plane position is set to an arbitrary position within the depth of field, the in-focus object plane position and the depth of field are switched by changing the position of the focus lens in the same manner as described above.

2.3. Change-in-Scene Detection Section

An example of the operation performed by the change-in-scene detection section 360 is described below. Note that the term "change in scene" used herein refers to a large change in color or contrast of the image acquired by the endoscope system. For example, the term "change in scene" used herein refers to a change in color or contrast of the image acquired by the endoscope system along with a change in structure of the object due to a change in observation position inside a digestive tract observed using the endoscope system, or a change in contrast of the object due to a pigment sprayed by the user. The term "change in scene" used herein excludes a change in contrast due to a change in focus, and a case where the color or the contrast of the image has changed to a large extent independently of a change in focus is referred to as "change in scene".

The change-in-scene detection section 360 receives the captured images that are sequentially output from the image processing section 330 at given time intervals, and calculates the amount of change in image signals between the captured images acquired at an arbitrary time interval. For example, the change-in-scene detection section 360 calculates the absolute value of the difference between the luminance signal of one of two captured images acquired at an arbitrary time interval and the luminance signal of the other captured image, calculates the sum of the absolute values within the image, and uses the calculated sum as the amount of change in image signals. Alternatively, the change-in-scene detection section 360 calculates the absolute value of the difference between the color difference signal of one of two captured images acquired at an arbitrary time interval and the color difference signal of the other captured image, calculates the sum of the absolute values within the image, and uses the calculated sum as the amount of change in image signals. The change-in-scene detection section 360 compares the calculated amount of change with a given threshold value, determines that no change in scene has occurred when the amount of change is smaller than the threshold value, and determines that a change in scene has occurred when the amount of change is larger than the threshold value. The change-in-scene detection section 360 sequentially outputs the change-in-scene information to the target in-focus position determination section 340 at arbitrary time intervals.

Note that the change-in-scene detection section 360 may perform a known motion detection process on the captured images acquired at an arbitrary time interval, and detect a change in scene based on the results of the motion detection process, for example. In this case, the change-in-scene detection section 360 may determine that a change in scene has occurred when the detected motion amount is equal to or larger than a threshold value, or when no motion has been detected, for example. Since it is considered that no motion is detected when the field of view of the endoscope system has moved to a large extent, and the observation target has changed, the change-in-scene detection section 360 determines that a change in scene has occurred when no motion has been detected.

2.4. Target in-Focus Position Determination Section

Figure 3:
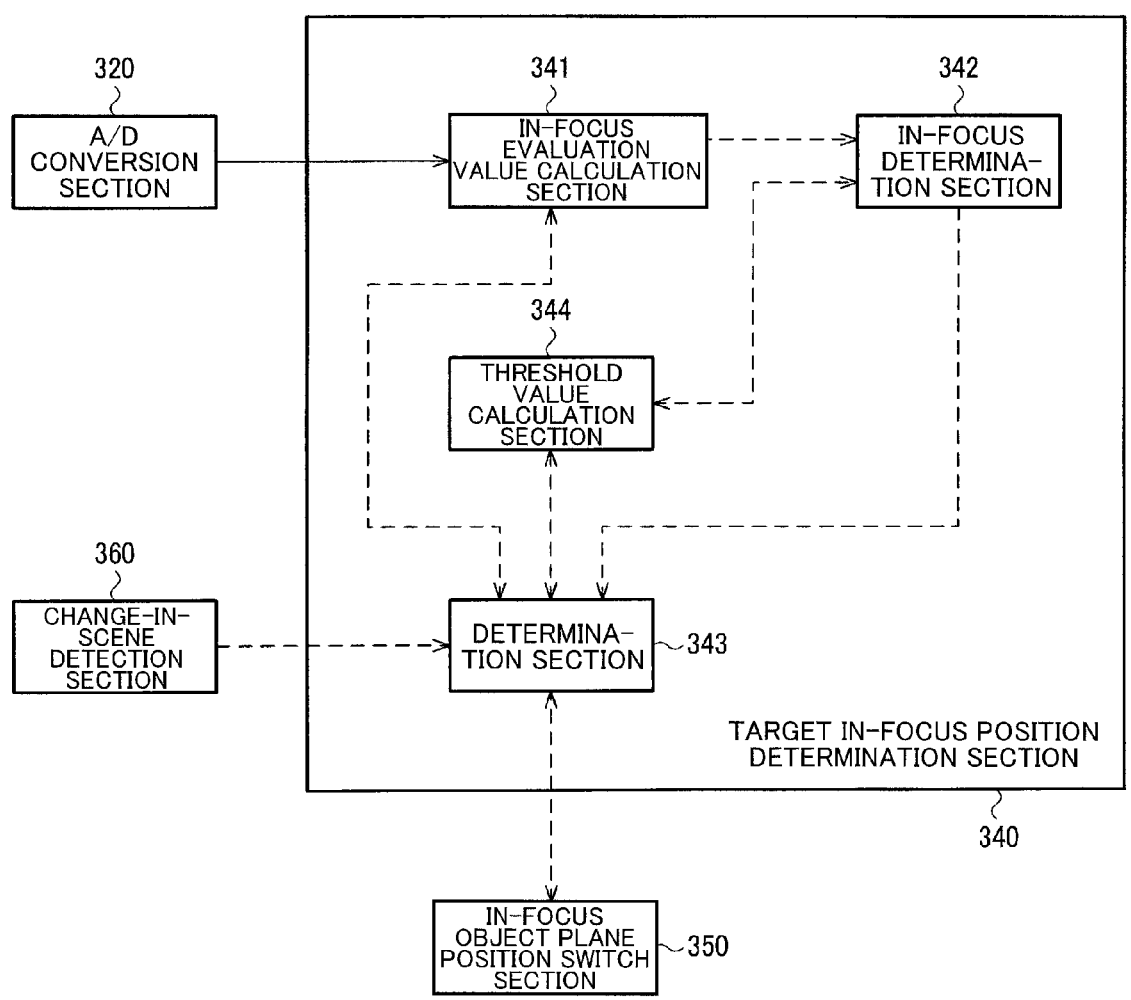
FIG. 3 illustrates a detailed configuration example of a target in-focus position determination section according to the first embodiment.

The details of the target in-focus position determination section 340 are described below. FIG. 3 illustrates a detailed configuration example of the target in-focus position determination section 340 according to the first embodiment. The target in-focus position determination section 340 includes an in-focus evaluation value calculation section 341, an in-focus determination section 342, a determination section 343, and a threshold value calculation section 344.

The operation of the target in-focus position determination section 340 when the change-in-scene information that indicates that no change in scene has occurred has been input from the change-in-scene detection section 360 is described below with reference to FIG. 4A.

In this case, the in-focus evaluation value calculation section 341 calculates in-focus evaluation values Val_Near and Val_Far that indicate the degree of in-focus from the captured image output from the A/D conversion section 320. The in-focus evaluation value Val_Near is the in-focus evaluation value when the in-focus object plane position NEAR has been selected, and the in-focus evaluation value Val_Far is the in-focus evaluation value when the in-focus object plane position FAR has been selected. For example, the in-focus evaluation value calculation section 341 sets an arbitrary evaluation area within the captured image, performs an arbitrary demosaicing process and an arbitrary HPF process on each pixel included in the evaluation area, and uses the sum of the HPF output value of each pixel as the in-focus evaluation value. The in-focus evaluation value calculation section 341 outputs the calculated in-focus evaluation values to the in-focus determination section 342.

The in-focus determination section 342 compares the in-focus evaluation values Val_Near and Val_Far output from the in-focus evaluation value calculation section 341 with an in-focus threshold value Th_Focus that is set in advance to determine whether or not the captured image is in an in-focus state or a defocused state. For example, the in-focus determination section 342 determines that the captured image is in an in-focus state when the in-focus evaluation values Val_Near and Val_Far are larger than the in-focus threshold value Th_Focus, and determines that the captured image is in a defocused state when the in-focus evaluation values Val_Near and Val_Far are smaller than the in-focus threshold value Th_Focus. The in-focus determination section 342 outputs in-focus determination information that indicates that the captured image is in an in-focus state or a defocused state to the determination section 343.

The determination section 343 determines the target in-focus position based on the in-focus determination information output from the in-focus determination section 342. Specifically, the determination section 343 determines the in-focus object plane position that is currently selected by the in-focus object plane position switch section 350 to be a new target in-focus position when the in-focus determination information output from the in-focus determination section 342 indicates that the captured image is in an in-focus state. The determination section 343 determines the in-focus object plane position that is not currently selected by the in-focus object plane position switch section 350 to be a new target in-focus position when the in-focus determination information indicates that the captured image is in a defocused state. The determination section 343 outputs the new target in-focus position to the in-focus object plane position switch section 350 as the target in-focus position information.

The operation of the target in-focus position determination section 340 when the change-in-scene information that indicates that a change in scene has occurred has been input from the change-in-scene detection section 360 is described below with reference to FIG. 4B.

In this case, the determination section 343 acquires the in-focus object plane position that is currently selected by the in-focus object plane position switch section 350. The in-focus evaluation value calculation section 341 calculates the in-focus evaluation values from the captured image output from the A/D conversion section 320 in the same manner as described above. The determination section 343 acquires the in-focus evaluation values from the in-focus evaluation value calculation section 341, and stores the in-focus object plane position and the in-focus evaluation values in a memory (not illustrated in the drawings) in a linked manner.

The determination section 343 then determines the in-focus object plane position that is not currently selected by the in-focus object plane position switch section 350 to be a new target in-focus position, and outputs the target in-focus position information to the in-focus object plane position switch section 350. The determination section 343 acquires the in-focus object plane position that is currently selected by the in-focus object plane position switch section 350, and checks whether or not the in-focus object plane position has been switched corresponding to the new target in-focus position. The in-focus evaluation value calculation section 341 calculates the in-focus evaluation values from the captured image output from the A/D conversion section 320 in the same manner as described above. The determination section 343 acquires the in-focus evaluation values from the in-focus evaluation value calculation section 341, and stores the in-focus object plane position and the in-focus evaluation values in the memory (not illustrated in the drawings) in a linked manner.

The in-focus evaluation value Val_Near when the in-focus object plane position NEAR is selected by the in-focus object plane position switch section 350, and the in-focus evaluation value Val_Far when the in-focus object plane position FAR is selected by the in-focus object plane position switch section 350 are acquired by the above operation.

The determination section 343 then compares the in-focus evaluation value Val_Near that corresponds to the in-focus object plane position NEAR with the in-focus evaluation value Val_Far that corresponds to the in-focus object plane position FAR, determines the in-focus object plane position that corresponds to the in-focus evaluation value Val_Near or Val_Far, whichever is larger, to be a new target in-focus position, and outputs the target in-focus position information to the in-focus object plane position switch section 350. The above operation makes it possible for the in-focus object plane position switch section 350 to select the in-focus object plane position NEAR or FAR that is in an in-focus state even when the change-in-scene detection section 360 has determined that a change in scene has occurred (i.e., when the color or the contrast of the image acquired by the endoscope system has changed to a large extent).

The threshold value calculation section 344 acquires at least one of the in-focus evaluation values Val_Near and Val_Far that respectively correspond to the in-focus object plane positions NEAR and FAR from the memory, and calculates a new in-focus threshold value Th_Focus New that is adapted to the current scene. The threshold value calculation section 344 outputs the calculated in-focus threshold value Th_Focus_New to the in-focus determination section 342, and the in-focus determination section 342 sets the in-focus threshold value Th_Focus New to be a new in-focus threshold value Th_Focus. First to third in-focus threshold value calculation methods are described below as examples of the in-focus threshold value calculation method.

2.5. In-Focus Threshold Value Calculation Method

The first in-focus threshold value calculation method is described below. The new in-focus threshold value Th_Focus_New is smaller than the in-focus evaluation value that corresponds to the in-focus object plane position selected to be in an in-focus state by the in-focus object plane position switch section 350. Therefore, the threshold value calculation section 344 acquires an in-focus evaluation value Val_Focus that corresponds to the newly selected in-focus object plane position from the memory, and calculates the new in-focus threshold value Th_Focus_New by the following expression (1). In FIG. 4B, Val_Focus=Val_Near when the target in-focus position is the in-focus object plane position NEAR, and Val_Focus=Val_Far when the target in-focus position is the in-focus object plane position FAR. Note that L is an arbitrary coefficient that satisfies 0<L<1.

$$Th\_Focus\_New = Val\_Focus * L \quad (1)$$

Figure 5:
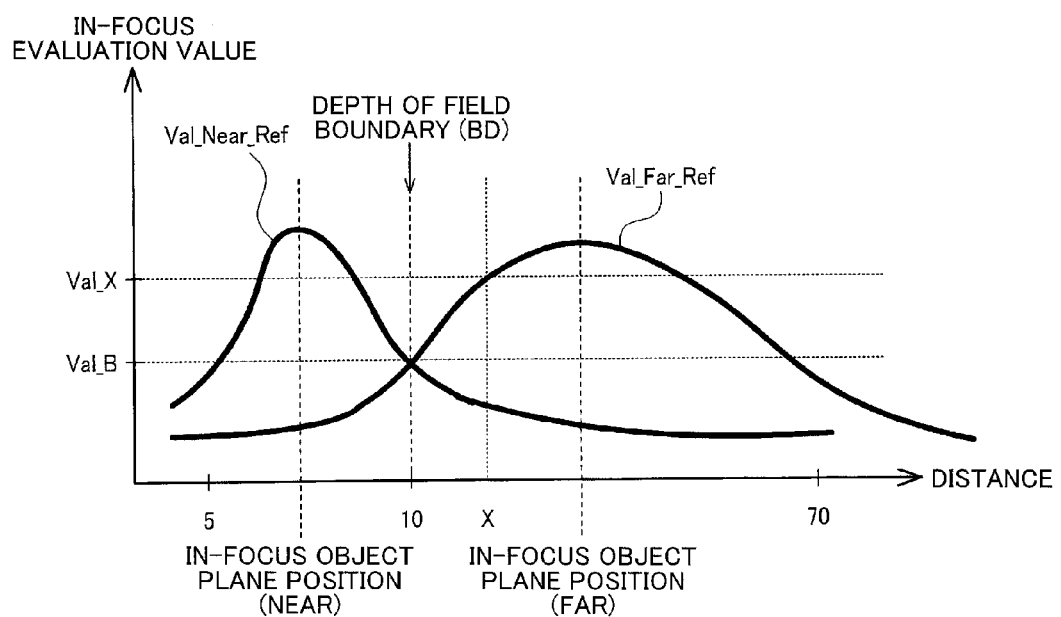
FIG. 5 is a view illustrating a second in-focus threshold value calculation method.

The second in-focus threshold value calculation method is described below with reference to FIG. 5. FIG. 5 is a view illustrating the relationship between the distance from the objective lens system 230 to the object and an in-focus evaluation value Val_Near_Ref when the in-focus object plane position NEAR is selected as the in-focus object plane position, and the relationship between the distance from the objective lens system 230 to the object and an in-focus evaluation value Val_Far_Ref when the in-focus object plane position FAR is selected as the in-focus object plane position.

The in-focus evaluation values Val_Near_Ref and Val_Far_Ref are relative in-focus evaluation values that indicate the characteristics of the in-focus evaluation value when the distance has changed. Specifically, the ratio of the in-focus evaluation value Val_Near_Ref and the in-focus evaluation value Val_Far_Ref does not change corresponding to the object, but the absolute value thereof changes corresponding to the object. The in-focus evaluation values Val_Near_Ref and Val_Far_Ref are acquired from the design data of the optical system, or acquired by measurement, for example.

As illustrated in FIG. 5, when the in-focus object plane position NEAR is selected as the in-focus object plane position, the in-focus evaluation value Val_Near_Ref becomes a maximum when the object lies at the in-focus object plane position NEAR, and decreases as the distance from the in-focus object plane position NEAR to the object increases. This also applies to the case where the in-focus object plane position FAR is selected as the in-focus object plane position. A position at which the distance from the objective lens system 230 to the object is about 10 mm is the boundary BD between the depth of field that corresponds to the in-focus object plane position NEAR and the depth of field that corresponds to the in-focus object plane position FAR, and the in-focus evaluation values Val_Near_Ref and Val_Far_Ref are (almost) identical values when the object lies at the boundary BD.

Since it is considered that the object is out of focus when the distance from the objective lens system 230 to the object has exceeded the boundary BD, a new threshold value is calculated based on an in-focus evaluation value Val_B that corresponds to the boundary BD. Specifically, the captured image is determined to be in a defocused state when the calculated in-focus evaluation value Val_Near (or Val_Far) is smaller than the in-focus evaluation value Val_B.

The absolute value of the in-focus evaluation value changes depending on the contrast of the object. However, the relationship between the distance and the in-focus evaluation values Val_Near_Ref and Val_Far_Ref (see FIG. 5) is determined by the imaging performance of the objective lens system 230, and changes to only a small extent depending on the contrast of the object. Therefore, the above relationship is calculated from the design data of the objective lens system 230, the results of experiments conducted using the endoscope system, or the like, and the distance and the in-focus evaluation values Val_Near_Ref and Val_Far_Ref are stored in a memory (not illustrated in the drawings) or the like in a linked manner in the form of an in-focus evaluation value table. The in-focus threshold value Th_Focus_New that is adapted to the current scene can be accurately calculated based on the in-focus evaluation values Val_Near and Val_Far acquired corresponding to the current scene.

Specifically, the ratio Val_Ratio of the in-focus evaluation values Val_Near and Val_Far acquired corresponding to the current scene is calculated by the following expression (2).

When Val_Near>Val_Far:

$$Val\_Ratio = Val\_Near/Val\_Far,$$

When Val_Near<Val_Far:

$$Val\_Ratio = Val\_Far/Val\_Near \qquad (2)$$

A calculation similar to that shown by the expression (2) is performed corresponding to each distance stored in the in-focus evaluation value table using the in-focus evaluation values Val_Near_Ref and Val_Far_Ref to calculate the ratio Val_Ratio_Ref corresponding to each distance. The ratio Val_Ratio is compared with the ratio Val_Ratio_Ref to search a distance at which the ratio Val_Ratio_Ref that is closest to the ratio Val_Ratio is obtained.

For example, when the distance X illustrated in FIG. 5 has been obtained as the search result, the in-focus threshold value Th_Focus_New that is adapted to the current scene is calculated by the following expression (3) using the in-focus evaluation value Val_Far acquired corresponding to the current scene, a value Val_X of the in-focus evaluation value Val_Far_Ref stored in the in-focus evaluation value table corresponding to the distance X, and a known value Val_B. Note that K is an arbitrary coefficient for adjusting the in-focus threshold value to be calculated.

$$Th\_Focus\_New = (Val\_Far * Val\_B * K)/Val\_X \qquad (3)$$

The above concept is similarly applied to the case where Val_Near>Val_Far. Specifically, the in-focus threshold value Th_Focus_New is calculated by the following expression (4) using the value of the in-focus evaluation value Val_Near_Ref stored in the in-focus evaluation value table corresponding to the distance X.

$$Th\_Focus\_New = (Val\_Near * Val\_B * K)/Val\_X \qquad (4)$$

The third in-focus threshold value calculation method is described below. According to the third in-focus threshold value calculation method, the threshold value calculation section 344 calculates the in-focus threshold value Th_Focus_New by the following expression (5). Note that M is an arbitrary coefficient for adjusting the in-focus threshold value to be calculated. An arbitrary weighted average value of the in-focus evaluation values Val_Near and Val_Far may also be used instead of applying the expression (5).

$$Th\_Focus\_New = \{(Val\_Near + Val\_Far)/2\} * M \qquad (5)$$

The endoscope system according to the first embodiment that performs the above AF control process can implement a high-accuracy AF operation even when a change in scene has occurred during screening examination by sequentially switching the in-focus object plane position to the in-focus object plane position NEAR and the in-focus object plane position FAR only immediately after the change in scene has occurred, and not sequentially switching the in-focus object plane position to the in-focus object plane position NEAR and the in-focus object plane position FAR thereafter during a period in which a change in scene does not occur. This makes it possible to implement an AF control process that minimizes a situation in which the observation target area for the user is out of focus, and is stable even if a change in contrast of the object has occurred.

The endoscope system according to the first embodiment can implement the in-focus determination process using an in-focus threshold value adapted to the current scene, even when the color or the contrast of the captured image has changed to a large extent due to a change in scene, by calculating the in-focus threshold value Th_Focus_New when a change in scene has been detected.

According to the first embodiment, the endoscope system includes the in-focus object plane position switch section 350, the target in-focus position determination section 340, and the change-in-scene detection section 360 (see FIG. 1).

As described above with reference to FIG. 2 and the like, the in-focus object plane position switch section 350 selects a first in-focus object plane position NEAR or a second in-focus object plane position FAR to switch the in-focus object plane position of the imaging section 200 to the first in-focus object plane position NEAR or the second in-focus object plane position FAR. The target in-focus position determination section 340 calculates the in-focus evaluation value Val_Near (or Val_Far) based on the captured image acquired by the imaging section 200, and determines the target in-focus position based on the in-focus evaluation value Val_Near (or Val_Far), the target in-focus position being the in-focus object plane position to which the in-focus object plane position of the imaging section 200 is switched by the in-focus object plane position switch section 350. The change-in-scene detection section 360 detects whether or not a change in scene has occurred based on the captured image.

As described above with reference to FIG. 4A and the like, the target in-focus position determination section 340 determines whether or not the in-focus evaluation value Val_Near (or Val_Far) satisfies a determination criterion until the change-in-scene detection section 360 detects that a change in scene has occurred, and selects the first in-focus object plane position NEAR or the second in-focus object plane position FAR that is not currently selected by the in-focus object plane position switch section 350 when the target in-focus position determination section 340 has determined that the in-focus evaluation value Val_Near (or Val_Far) does not satisfy the determination criterion (defocused state).

According to the above configuration, the in-focus determination process can be performed using only the in-focus evaluation value that corresponds to the selected in-focus object plane position until the subsequent change in scene is detected after a change in scene has been detected. Therefore, since it suffices to switch the in-focus object plane position only when it has been determined that the captured image is in a defocused state, the switch frequency can be reduced. If the in-focus object plane position is switched, and the two in-focus evaluation values are acquired each time the AF process is performed, a defocused image may be displayed each time the AF process is performed. According to the first embodiment, since the in-focus object plane position is not switched until it is determined that the captured image is in a defocused state (i.e., the object is out of focus), it is possible to reduce the possibility that a defocused image is displayed.

Note that the term "in-focus evaluation value" used herein refers to a value or information used to determine whether or not the object in the captured image is in focus. For example, the contrast value is used as the in-focus evaluation value when using the contrast AF process. The contrast value is calculated by extracting a high-frequency component of the image, for example. Note that the in-focus evaluation value is not limited to the contrast value. Specifically, it suffices that the in-focus evaluation value be an evaluation value that becomes a maximum at the position of the object plane when the image plane coincides with the image plane of the image sensor, and decreases as the distance from the position of the object plane increases.

The term "change in scene" used herein refers to a change in color or contrast of the image due to a change in object, or a change in color or contrast of the image due to a procedure operation performed on the object, and excludes a decrease in contrast due to a change in focus. A change in scene may be a change in imaging condition due to a change in imaging mode, a change in image processing, or the like (described later in connection with a second embodiment), for example. A change in object includes a change in imaging range (imaging target) due to the movement of the imaging section or the motion of the object, a change (e.g., bleeding) in object within an identical imaging range due to procedures performed on the affected area, and the like. A user operation performed on the object includes various operations performed during diagnosis and procedures using an endoscope, such as a water/medicine discharge operation, a water/body fluid suction operation, and a procedure operation (e.g., excision).

As described above with reference to FIG. 4B and the like, the target in-focus position determination section 340 may update the determination criterion (e.g., threshold value Th_Focus) when the change-in-scene detection section 360 has detected that a change in scene has been occurred.

Since it is considered that the color or the contrast of the image changes, and the in-focus evaluation value also changes when a change in scene has occurred, the in-focus determination accuracy may deteriorate if an identical determination criterion is used independently of the scene. According to the above configuration, since the determination criterion corresponding to a new scene can be set when a change in scene has occurred, it is possible to implement a highly accurate in-focus determination process corresponding to a change in scene.

As described above with reference to FIG. 4B and the like, the target in-focus position determination section 340 may sequentially select the first in-focus object plane position NEAR and the second in-focus object plane position FAR when the change-in-scene detection section 360 has detected that a change in scene has been occurred, and calculate a first in-focus evaluation value Val_Near that is an in-focus evaluation value at the first in-focus object plane position NEAR, and a second in-focus evaluation value Val_Far that is an in-focus evaluation value at the second in-focus object plane position FAR. The in-focus evaluation value is an evaluation value that increases as the degree of in-focus increases. The target in-focus position determination section 340 may determine the first in-focus object plane position NEAR to be the target in-focus position when the first in-focus evaluation value Val_Near is larger than the second in-focus evaluation value Val_Far, and determine the second in-focus object plane position FAR to be the target in-focus position when the second in-focus evaluation value Val_Far is larger than the first in-focus evaluation value Val_Near.

Since it is considered that the in-focus evaluation value changes when a change in scene has occurred, the in-focus object plane position may not be determined immediately after a change in scene has occurred using only one in-focus evaluation value that corresponds to the first in-focus object plane position NEAR or the second in-focus object plane position FAR. According to the above configuration, the in-focus evaluation values Val_Near and Val_Far that respectively correspond to the first in-focus object plane position NEAR and the second in-focus object plane position FAR are acquired when a change in scene has been detected, and the in-focus evaluation values Val_Near and Val_Far are compared to determine the target in-focus position. This makes it possible to determine the in-focus object plane position immediately after a change in scene has occurred.

As described above with reference to FIG. 4A and the like, the determination criterion may be a condition whereby the in-focus evaluation value Val_Near (or Val_Far) is larger than the threshold value Th_Focus. As described above with reference to FIG. 4B and the like, the target in-focus position determination section 340 may update the threshold value Th_Focus (calculate the threshold value Th_Focus_New) based on at least one of the first in-focus evaluation value Val_Near and the second in-focus evaluation value Val_Far.

According to the above configuration, the threshold value can be updated corresponding to the in-focus evaluation value of the image acquired after a change in scene has occurred. An in-focus determination process using the determination criterion corresponding to a change in scene can be implemented by performing the in-focus determination process using the updated threshold value.

As described above with reference to the expression (1), the target in-focus position determination section 340 may multiply the first in-focus evaluation value Val_Near by a given coefficient L that is smaller than 1 to calculate the threshold value Th_Focus_New when the first in-focus evaluation value Val_Near is larger than the second in-focus evaluation value Val_Far, and multiply the second in-focus evaluation value Val_Far by the given coefficient L to calculate the threshold value Th_Focus_New when the second in-focus evaluation value Val_Far is larger than the first in-focus evaluation value Val_Near.

According to the above configuration, the first in-focus object plane position NEAR or the second in-focus object plane position FAR that corresponds to the first in-focus evaluation value Val_Near or the second in-focus evaluation value Val_Far, whichever is larger, can be selected as the in-focus object plane position of the imaging section 200, and the threshold value Th_Focus (Th_Focus_New) can be determined from the in-focus evaluation value that corresponds to the selected in-focus object plane position. This makes it possible to determine the threshold value that is appropriate for the in-focus determination process on the image acquired after a change in scene has occurred.

As described above with reference to FIG. 5 and the like, the endoscope system may include a storage section (i.e., a memory not illustrated in the drawings) that stores characteristic information Val_Near_Ref about the first in-focus evaluation value and characteristic information Val_Far_Ref about the second in-focus evaluation value when the distance to the object is changed in the form of a table. As described above with reference to the expression (2), the target in-focus position determination section 340 may calculate the ratio Val_Ratio of the first in-focus evaluation value Val_Near and the second in-focus evaluation value Val_Far. As described above with reference to the expressions (3) and (4), the target in-focus position determination section 340 may search the table based on the ratio Val_Ratio to estimate the in-focus evaluation value (Val_Far*Val_B)Val_X (or (Val_Near*Val_B)/Val_X) when the first in-focus evaluation value Val_Near is equal to the second in-focus evaluation value Val_Far, and multiply the estimated in-focus evaluation value by a given coefficient K to calculate the threshold value Th_Focus_New.

According to the above configuration, the threshold value Th_Focus (Th_Focus_New) can be determined from the in-focus evaluation value when the first in-focus evaluation value Val_Near is equal to the second in-focus evaluation value Val_Far. The in-focus determination process is performed using the determined threshold value to determine that the captured image is in a defocused state (i.e., the object is out of focus) when movement from the depth of field boundary BD toward the second in-focus object plane position FAR has occurred when the first in-focus object plane position NEAR is selected, and determine that the captured image is in a defocused state (i.e., the object is out of focus) when movement from the depth of field boundary BD toward the first in-focus object plane position NEAR has occurred when the second in-focus object plane position FAR is selected. This makes it possible to implement a highly accurate in-focus determination process that takes account of the depth of field boundary between the in-focus object plane positions.

The change-in-scene detection section 360 may detect whether or not a change in scene has occurred by comparing the image signals (e.g., luminance signals or color difference signals) of a first captured image among a plurality of captured images sequentially acquired by the imaging section 200 with the image signals of a second captured image acquired prior to the first captured image. More specifically, the change-in-scene detection section 360 may calculate the amount of change (e.g., the absolute value of the difference in luminance signals or the absolute value of the difference in color difference signals) between the image signals of the first captured image and the image signals of the second captured image, and determine that a change in scene has occurred when the amount of change is larger than a threshold value.

This makes it possible to detect a change in color or contrast from the captured image when the color or the contrast of the image has changed due to a change in scene to detect that a change in scene has occurred.

The change-in-scene detection section 360 may detect whether or not a change in scene has occurred based on the result of motion detection between the first captured image and the second captured image.

According to the above configuration, a change in scene can be detected by detecting a change in imaging range due to the movement of the imaging section or the motion of the object through motion detection. For example, it is determined that the imaging range has changed when no motion has been detected, and it is determined that a change in scene has occurred.

3. Second Embodiment 3.1. Endoscope system

Figure 6:
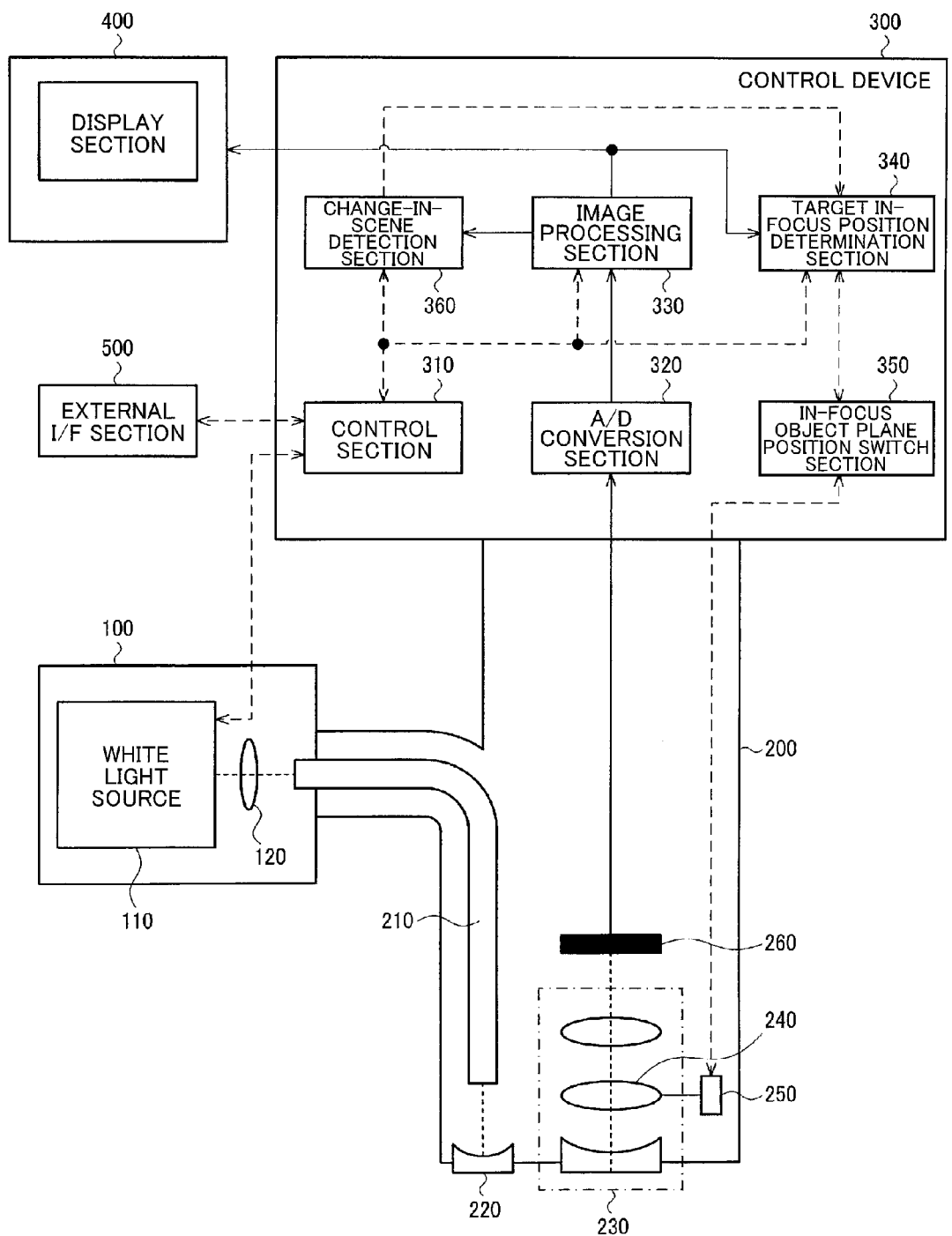
FIG. 6 illustrates a configuration example of an endoscope system according to a second embodiment.

FIG. 6 illustrates a configuration example of an endoscope system according to the second embodiment. The endoscope system illustrated in FIG. 6 includes a light source section 100, an imaging section 200, a control device 300 (processing section), a display section 400, and an external I/F section 500. Note that the same elements as those described above in connection with the first embodiment are respectively indicated by the same reference signs, and description thereof is appropriately omitted.

The A/D conversion section 320 converts the analog image signals sequentially output from the image sensor 260 into digital image signals, and sequentially outputs the digital image signals to the image processing section 330. The image processing section 320 performs image processing (e.g., white balance process, interpolation process (demosaicing process), color conversion process, grayscale transformation process, contrast enhancement process, and noise reduction process) on the image signals output from the AD conversion section 320, and sequentially outputs the resulting image signals to the target in-focus position determination section 340, the change-in-scene detection section 360, and the display section 400.

The external I/F section 500 is an interface that allows the user to perform an input operation or the like on the endoscope system. The external I/F section 500 includes a start button (imaging start/stop button), an AF start/stop button, an observation mode (normal light observation or special light observation) switch button, a contrast enhancement adjustment button, a noise reduction adjustment button, an adjustment button for adjusting the imaging condition or the image processing parameter, and the like.

The endoscope system according to the second embodiment is configured to observe a digestive tract while switching the observation mode (state) between normal light observation that utilizes white light and special light observation that enhances a specific wavelength band to enhance the contrast of the object. The observation mode is switched between normal light observation and special light observation by switching the illumination light emitted from the light source section 100 between white light and special light (NBI described later), for example. Alternatively, the light source section 100 may emit white light, and the image processing section 330 may acquire a normal light image and a special light image by performing image processing (FICE described later). The details of normal light observation and special light observation are described later.

3.2. Change-in-Scene Detection Section

An example of the operation performed by the change-in-scene detection section 360 is described below. Note that the term "change in scene" used in connection with the second embodiment refers to a change in imaging condition. For example, the term "change in scene" used in connection with the second embodiment refers to a change in observation mode (normal light observation or special light observation), a change in the degree of image contrast enhancement, a change in the degree of noise reduction, and the like. Even when the contrast of the object does not change, the color or the contrast of the image acquired by the endoscope system changes to a large extent due to a change in imaging condition. Therefore, a change in imaging condition is detected as a change in scene.

When the user has changed the imaging condition via the external I/F section 500, the control section 310 outputs the details of the change in imaging condition to the change-in-scene detection section 360 as imaging condition change information.

The change-in-scene detection section 360 determines that a change in scene has not occurred when the imaging condition change information has not been output from the control section 310, and determines that a change in scene has occurred when the imaging condition change information has been output from the control section 310 The change-in-scene detection section 360 outputs information that indicates the presence or absence of a change in scene to the target in-focus position determination section 340 as the change-in-scene information at arbitrary time intervals. When the change-in-scene detection section 360 outputs the change-in-scene information indicates that a change in scene has occurred, the change-in-scene detection section 360 outputs the details of the change in imaging condition to the target in-focus position determination section 340 together with the change-in-scene information.

3.3. Target in-Focus Position Determination Section

Figure 7:
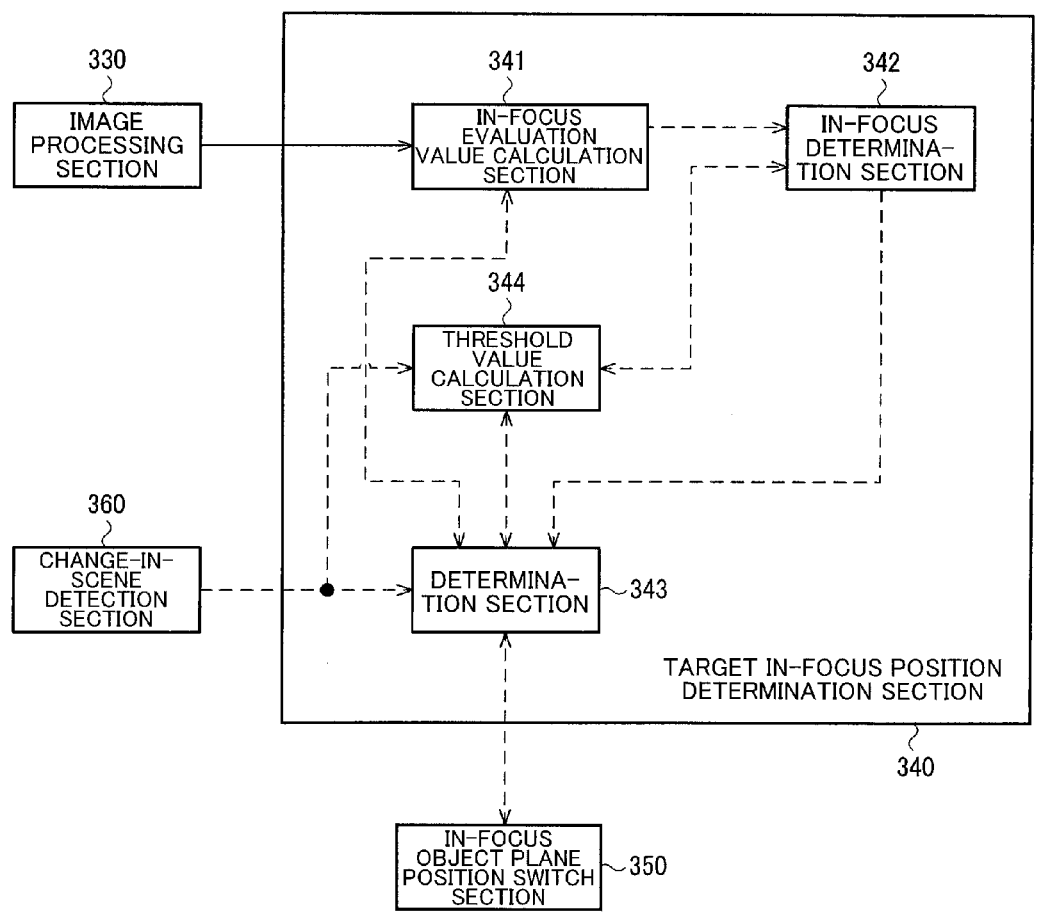
FIG. 7 illustrates a detailed configuration example of a target in-focus position determination section according to the second embodiment.

The details of the target in-focus position determination section 340 are described below. FIG. 7 illustrates a detailed configuration example of the target in-focus position determination section 340 according to the second embodiment. The target in-focus position determination section 340 includes an in-focus evaluation value calculation section 341, an in-focus determination section 342, a determination section 343, and a threshold value calculation section 344. Note that the same elements as those described above in connection with the first embodiment are respectively indicated by the same reference signs, and description thereof is appropriately omitted.

The in-focus evaluation value calculation section 341 calculates the in-focus evaluation value that indicates the degree of in-focus based on the captured image output from the image processing section 330. For example, the in-focus evaluation value calculation section 341 sets an arbitrary evaluation area within the captured image, performs an arbitrary HPF process on each pixel included in the evaluation area, and uses the sum of the HPF output value of each pixel as the in-focus evaluation value.

The operation of the target in-focus position determination section 340 when the change-in-scene information that indicates that a change in scene has occurred has been input from the change-in-scene detection section 360 is described below. Note that the operation of the target in-focus position determination section 340 when a change in scene has not occurred is the same as described above in connection with the first embodiment.

The target in-focus position determination section 340 calculates the in-focus threshold value Th_Focus in the same manner as in the first embodiment. Specifically, when the change-in-scene detection section 360 has detected that a change in scene has occurred based on a change in contrast of the object, the target in-focus position determination section 340 calculates the in-focus threshold value Th_Focus_New using any of the above first to third calculation methods, and the in-focus determination section 342 uses the new in-focus threshold value Th_Focus_New as the in-focus threshold value Th_Focus.

When the change-in-scene detection section 360 has detected that a change in scene has occurred from a change in imaging condition when the in-focus threshold value Th_Focus is set, the threshold value calculation section 344 acquires the current in-focus threshold value Th_Focus from the in-focus determination section 342, and calculates the in-focus threshold value Th_Focus_New based on the in-focus threshold value Th_Focus. The target in-focus position determination section 340 maintains the current target in-focus position without switching the target in-focus position between the in-focus object plane positions NEAR and FAR, and switches the target in-focus position based on the in-focus determination process using the updated in-focus threshold value Th_Focus. When the change-in-scene detection section 360 has detected that a change in scene has occurred from the captured image, the target in-focus position determination section 340 determines the target in-focus position while switching the target in-focus position between the in-focus object plane positions NEAR and FAR in the same manner as in the first embodiment.

A fourth in-focus threshold value calculation method is described below as an example of the in-focus threshold value calculation method. The threshold value calculation section 344 calculates the in-focus threshold value Th_Focus_New by the following expression (6). Note that the coefficient M is an arbitrary value calculated by the threshold value calculation section 344 corresponding to the details of the change in imaging condition output from the change-in-scene detection section 360.

$$Th\_Focus\_New = Th\_Focus * M \qquad (6)$$

The threshold value calculation section 344 calculates the coefficient M as described below. Specifically, the degree of change in in-focus evaluation value corresponding to a change in imaging condition is estimated in advance from the results of experiments using the endoscope system, for example. The ratio of a change in in-focus evaluation value relative to a change in imaging condition is stored in a memory (not illustrated in the drawings) as the coefficient M corresponding to the details of a change in imaging condition. This makes it possible to change the in-focus threshold value to a value corresponding to the details of a change in imaging condition even when the user has changed the imaging condition during screening examination, and the in-focus determination section 342 can implement an accurate in-focus determination process.

The endoscope system according to the second embodiment that performs the above AF control process can implement a high-accuracy AF operation even when a change in scene has occurred during screening examination by utilizing the new in-focus threshold value Th_Focus_New as the in-focus threshold value Th_Focus without sequentially switching the in-focus object plane position to the in-focus object plane position NEAR and the in-focus object plane position FAR, since a change in optical in-focus state does not occur when the change in scene has occurred due to a change in imaging condition. The endoscope system according to the second embodiment can implement a high-accuracy AF operation by sequentially switching the in-focus object plane position to the in-focus object plane position NEAR and the in-focus object plane position FAR only immediately after a change in scene has occurred due to a change other than a change in imaging condition, and not sequentially switching the in-focus object plane position to the in-focus object plane position NEAR and the in-focus object plane position FAR thereafter during a period in which a change in scene does not occur due to a change other than a change in imaging condition. This makes it possible to implement an AF control process that minimizes a situation in which the observation target area for the user is out of focus, and is stable even if a change in contrast of the image has occurred due to a change in imaging condition.

The endoscope system according to the second embodiment can implement the in-focus determination process using an in-focus threshold value adapted to the current scene, even when the color or the contrast of the captured image has changed to a large extent due to a change in scene, by calculating the in-focus threshold value Th_Focus_New using the above method.

3.4. Special Light Observation

Figure 8:
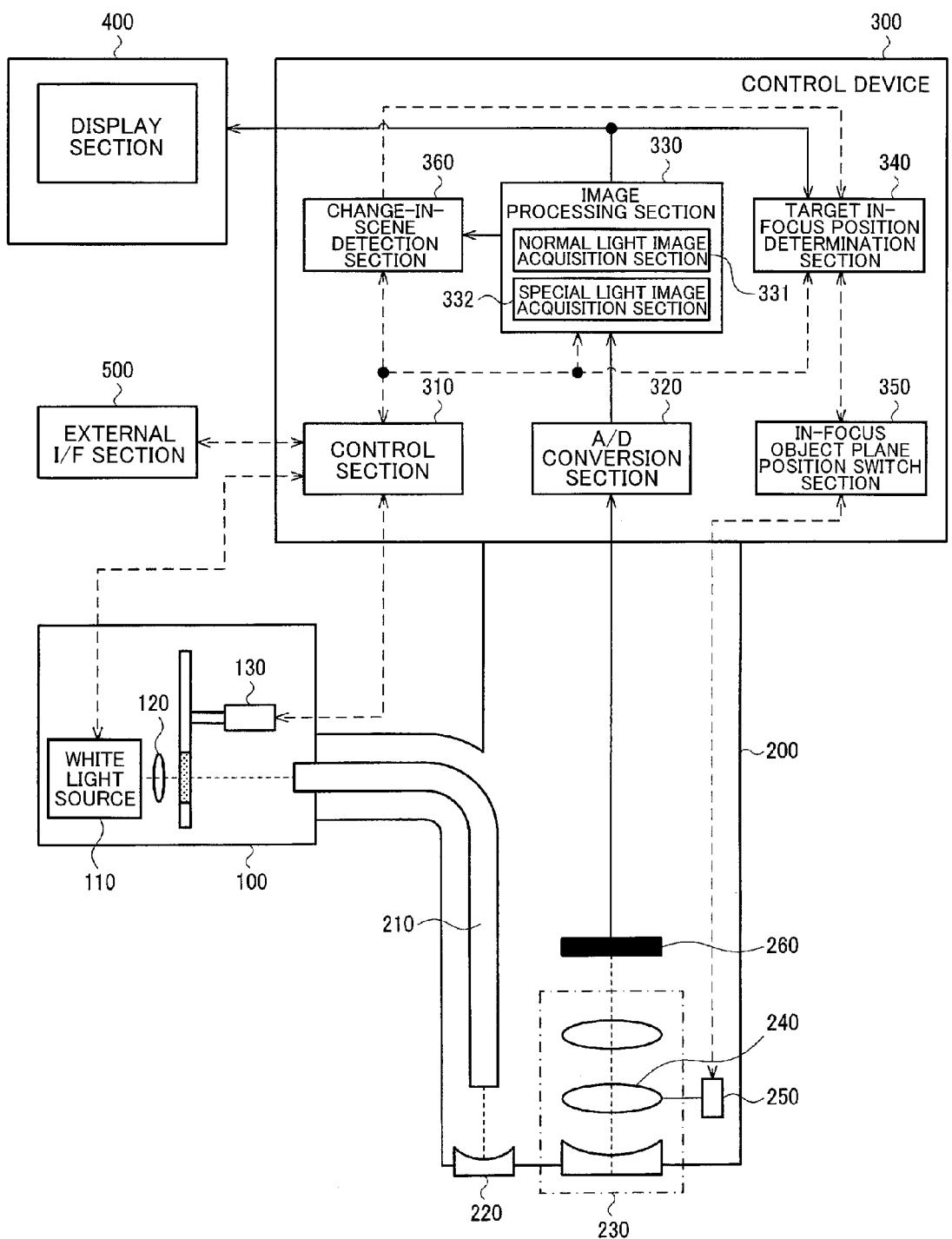
FIG. 8 illustrates a configuration example of an endoscope system when implementing special light observation.

FIG. 8 illustrates a configuration example of the endoscope system when implementing special light observation. The endoscope system illustrated in FIG. 8 includes a light source section 100, an imaging section 200, a control device 300 (processing section), a display section 400, and an external I/F section 500. An image processing section 330 includes a normal light image acquisition section 331 and a special light image acquisition section 332. Note that the same elements as those described above with reference to FIG. 1 or 6 are respectively indicated by the same reference signs, and description thereof is appropriately omitted.

The light source section 100 includes a white light source 110 that emits white light, a condenser lens 120 that focuses the white light emitted from the white light source 110 on a light guide fiber 210, and a rotary filter 130 that extracts light within a specific wavelength band from the white light.

Figure 9:
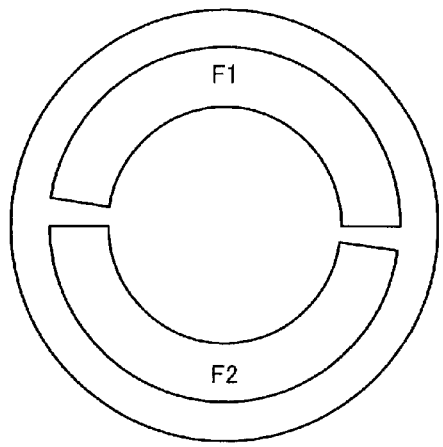
FIG. 9 illustrates a detailed configuration example of a rotary filter.
Figure 10:
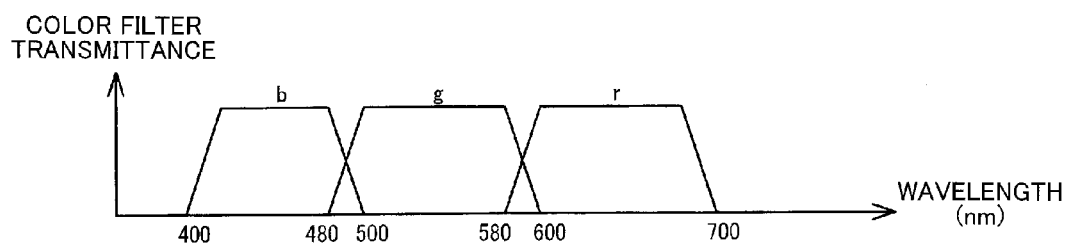
FIG. 10 illustrates an example of the transmittance characteristics of a filter F1 included in a rotary filter.
Figure 11:
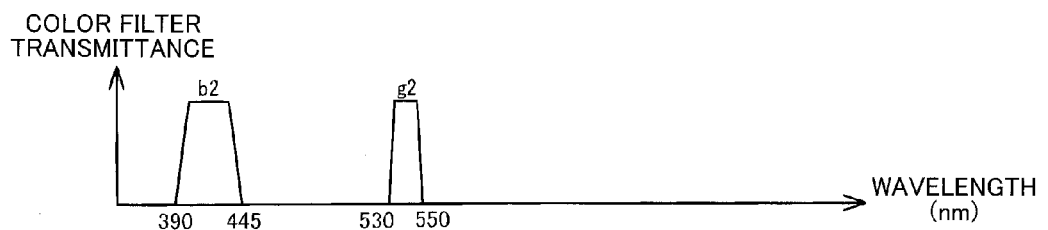
FIG. 11 illustrates an example of the transmittance characteristics of a filter F2 included in a rotary filter.

As illustrated in FIG. 9, the rotary filter 130 includes two color filters F1 and F2 that differ in transmittance characteristics. As illustrated in FIG. 10, the filter F1 allows light within the wavelength band of white light to pass through. For example, the filter F1 allows light within a wavelength band of 400 to 700 nm to pass through. The passband of the filter F1 may be divided into the band b of blue light B, the band g of green light G, and the band r of red light R (see FIG. 10), or may be a continuous band of 400 to 700 nm. As illustrated in FIG. 11, the filter F2 allows light within the wavelength band of special light (i.e., a specific wavelength band that is narrower than the wavelength band of white light) to pass through. For example, the filter F2 allows light within the wavelength band g2 of first narrow-band light G2 and the wavelength band b2 of second narrow-band light B2 to pass through. The wavelength band g2 is 530 to 550 nm, and the wavelength band b2 is 390 to 445 nm.

The control section 310 controls the rotation of the rotary filter 130, to sequentially apply the white light that has passed through the filter F1 and the narrow-band light that has passed through the filter F2 to the object. The object to which the white light is applied and the object to which the narrow-band light is applied are captured by the image sensor 260. The A/D conversion section 320 subjects the image signals obtained by the image sensor 260 to A/D conversion, and outputs the resulting image signals to the normal light image acquisition section 331 and the special light image acquisition section 332.

The normal light image acquisition section 331 generates a normal light image from the image signals captured when applying the white light. Specifically, the normal light image acquisition section 331 performs image processing (e.g., interpolation process, white balance process, color conversion process, and grayscale transformation process) on the image signals to generate a normal light image.

The special light image acquisition section 332 generates a special light image from the image signals captured when applying the special light. The special light image is a narrow-band light image. The special light includes the first narrow-band light G2 and the second narrow-band light B2 (see FIG. 11). For example, when the image sensor 260 is an RGB Bayer array image sensor, the first narrow-band light G2 is captured by green (G) pixels, and the second narrow-band light B2 is captured by blue (B) pixels. The special light image acquisition section 332 performs an interpolation process on the G2 pixel values and the B2 pixel values to generate a G2 image and a B2 image. The special light image acquisition section 332 generates an RGB color image by inputting the G2 image to the R channel, and inputting the B2 image to the G channel and the B channel. The color image thus generated is the special light image.

When the user has selected normal light observation via the external I/F section 500, the target in-focus position determination section 340 performs the focus control process using the normal light image, and the display section 400 displays the normal light image under control of the control section 310. When the user has selected special light observation via the external I/F section 500, the target in-focus position determination section 340 performs the focus control process using the special light image, and the display section 400 displays the special light image under control of the control section 310.

When the imaging condition change information that indicates that the observation mode has been switched between normal light observation and special light observation has been input from the control section 310, the change-in-scene detection section 360 determines that a change in scene has occurred, and outputs the change-in-scene information to the target in-focus position determination section 340. The target in-focus position determination section 340 receives the change-in-scene information, and updates the in-focus threshold value Th_Focus in the same manner as described above.

Although an example has been described above in which the normal light image and the special light image are sequentially captured while rotating the rotary filter 130, and the normal light image or the special light image is displayed on the display section 400 corresponding to selection by the user, another configuration may also be employed. For example, the normal light image may be captured in a state in which the filter F1 is inserted when the user has selected normal light observation, and the special light image may be captured in a state in which the filter F2 is inserted when the user has selected special light observation.

Although an example has been described above in which the rotary filter 130 includes the filter F1 that allows the white light to pass through, and the filter F2 that allows the special light to pass through, another configuration may also be employed. For example, the rotary filter 130 may include five filters that respectively allow R light, G light, B light, G2 light, and B2 light to pass through. In this case, an R image, a G image, a B image, a G2 image, and a B2 image may be sequentially captured using a monochrome image sensor while rotating the rotary filter 130, the normal light image may be generated from the R image, the G image, and the B image, and the special light image may be generated from the G2 image and the B2 image.

According to the second embodiment, the endoscope system includes the control section 310 that changes the imaging condition for the captured image. The change-in-scene detection section 360 determines that a change in scene has occurred when the change-in-scene detection section 360 has detected that the imaging condition have been changed by the control section 310.

It is possible to implement a highly accurate in-focus determination process corresponding to a change in scene even when the color or the contrast of the image changes due to a change in imaging condition by detecting a situation in which the imaging condition have been changed by the control section 310 as a change in scene. Specifically, a change in scene can be detected from the control signal instead of detecting a change in scene from the image.

Note that the term "change in imaging condition" used herein refers to a change in imaging condition that affects the captured image in-focus evaluation value used for the focus control process (e.g., a change in imaging condition that causes a change in color or contrast of the image), and includes a change in observation mode, a change in image processing, and the like. The term "change in scene" excludes a decrease in contrast due to a change in focus, and the term "change in imaging condition" exclude a change in focus. The imaging condition are changed by the user via the external I/F section 500, for example. Alternatively, the imaging condition may be changed by the control process performed by the control section 310. The term "change in imaging condition" includes a change in illumination light, a change in exposure conditions, and a change in zoom magnification setting mode or the like. The term "change in image processing" includes a change in grayscale characteristics (grayscale transformation process), a change in color conversion characteristics (color conversion process), a change in the degree of noise reduction (noise reduction process), a change in the degree of contrast enhancement (contrast enhancement process), and the like.

As described above with reference to FIGS. 8 to 11, the observation mode may include a normal light observation mode in which the normal light image is captured, and a special light observation mode in which the special light image is captured, the normal light image being an image that includes information within the wavelength band of white light, and the special light image being an image that includes information within the specific wavelength band.

It is considered that the normal light image and the special light image differ in color or contrast since the normal light image and the special light image differ in wavelength band. According to the second embodiment, since it is detected that a change in scene has occurred when the observation mode has been switched between the normal light observation mode and the special light observation mode, the in-focus determination process can be performed while setting the determination conditions corresponding to the normal light image and the special light image.

The specific wavelength band may be a band that is narrower than the wavelength band (e.g., 380 to 650 nm) of white light. For example, the normal light image and the special light image may be in vivo images, and the specific wavelength band included in the in vivo images may be the wavelength band of light absorbed by hemoglobin in blood. The wavelength band of light absorbed by hemoglobin may be 390 to 445 nm (first narrow-band light or the B2 component of narrow-band light) or 530 to 550 nm (second narrow-band light or the G2 component of narrow-band light), for example.

This makes it possible to implement narrow band imaging (NBI), and observe the structure of the surface area of tissue and blood vessels situated in a deep area. A lesion area (e.g., epidermoid cancer) that is difficult to observe using normal light can be displayed in brown or the like by inputting the resulting signals to given channels (G2→R, B2→G and B), so that the lesion area can be reliably detected. A wavelength band of 390 to 445 nm or 530 to 550 nm is selected from the viewpoint of absorption by hemoglobin and the ability to reach the surface area or the deep area of tissue. Note that the wavelength band is not limited thereto. For example, the lower limit of the wavelength band may decrease by about 0 to 10%, and the upper limit of the wavelength band may increase by about 0 to 10%, depending on a variation factor (e.g., experimental results for absorption by hemoglobin and the ability to reach the surface area or the deep area of tissue).

The endoscope system may include a special light image acquisition section that generates the special light image based on the acquired normal light image. For example, the endoscope system illustrated in FIG. 8 may be configured so that the rotary filter 130 is omitted, the light source section 100 emits white illumination light, and the special light image acquisition section 332 acquires the normal light image from the normal light image acquisition section 331, and generates the special light image from the acquired normal light image.

More specifically, the special light image acquisition section 332 may include a signal extraction section that extracts signals within the wavelength band of white light from the acquired normal light image. The special light image acquisition section 332 may generate the special light image that includes signals within the specific wavelength band based on the extracted signals within the wavelength band of white light. For example, the signal extraction section may estimate the spectral reflectivity characteristics of the object from the RGB signals of the normal light image at intervals of 10 nm, and the special light image acquisition section 332 may integrate the estimated signal components within the specific wavelength band to generate the special light image.

More specifically, the special light image acquisition section 332 may include a matrix data setting section that sets matrix data for calculating the signals within the specific wavelength band from the signals within the wavelength band of white light. The special light image acquisition section 332 may calculate the signals within the specific wavelength band from the signals within the wavelength band of white light using the matrix data set by the matrix data setting section to generate the special light image. For example, the matrix data setting section may set table data as the matrix data, the spectral characteristics of illumination light within the specific wavelength band being stored in the table data at intervals of 10 nm. The special light image acquisition section 332 may multiply the estimated spectral reflectivity characteristics of the object by the spectral characteristics (coefficient) stored in the table data, and may perform the integration process to generate the special light image.

According to the above configuration, since the special light image can be generated based on the normal light image, it is possible to implement the system using only one light source that emits the normal light and one image sensor that captures the normal light. This makes it possible to reduce the size of a capsule endoscope or the size of the insertion section of a scope-type endoscope. Moreover, a reduction in cost can be achieved since the number of parts can be reduced.

Although only some embodiments of the invention and the modifications thereof have been described in detail above, those skilled in the art will readily appreciate that many modifications are possible in the embodiments and the modifications thereof without materially departing from the novel teachings and advantages of the invention. A plurality of elements described in connection with the above embodiments and the modifications thereof may be appropriately combined to implement various configurations. For example, some of the elements described in connection with the above embodiments and the modifications thereof may be omitted. Some of the elements described in connection with different embodiments or modifications thereof may be appropriately combined. Specifically, various modifications and applications are possible without materially departing from the novel teachings and advantages of the invention.

Any term cited with a different term having a broader meaning or the same meaning at least once in the specification and the drawings can be replaced by the different term in any place in the specification and the drawings.

What is claimed is:

1. An endoscope system comprising:
    an in-focus object plane position switch that selects a first in-focus object plane position or a second in-focus object plane position to switch an in-focus object plane position of an imaging section to the first in-focus object plane position or the second in-focus object plane position;
    a controller comprising hardware, the controller comprising:
        a target in-focus position determination section that calculates an in-focus evaluation value based on a captured image acquired by the imaging section, and determines a target in-focus position based on the in-focus evaluation value, the target in-focus position being the in-focus object plane position to which the in-focus object plane position of the imaging section is switched by the in-focus object plane position switch; and
        a change-in-scene detection section that detects whether or not a change in scene has occurred based on the captured image,
        the target in-focus position determination section determining whether or not the in-focus evaluation value satisfies a determination criterion until the change-in-scene detection section detects that the change in scene has occurred, and selecting the first in-focus object plane position or the second in-focus object plane position that is not currently selected by the in-focus object plane position switch to be the target in-focus position when the target in-focus position determination section has determined that the in-focus evaluation value does not satisfy the determination criterion;
    wherein the target in-focus position determination section updating the determination criterion when the change-in-scene detection section has detected that the change in scene has occurred.

2. The endoscope system as defined in claim 1, wherein:
    the target in-focus position determination section sequentially selecting the first in-focus object plane position and the second in-focus object plane position when the change-in-scene detection section has detected that the change in scene has occurred, and calculating a first in-focus evaluation value at the first in-focus object plane position and a second in-focus evaluation value at the second in-focus object plane position as the in-focus evaluation value that increases as a degree of in-focus increases, and
    the target in-focus position determination section determining the first in-focus object plane position to be the target in-focus position when the first in-focus evaluation value is larger than the second in-focus evaluation value, and determining the second in-focus object plane position to be the target in-focus position when the second in-focus evaluation value is larger than the first in-focus evaluation value.

3. The endoscope system as defined in claim 2, wherein:
    the determination criterion being a condition whereby the in-focus evaluation value is larger than a threshold value, and
    the target in-focus position determination section updating the threshold value based on at least one of the first in-focus evaluation value and the second in-focus evaluation value.

4. The endoscope system as defined in claim 3, wherein the target in-focus position determination section multiplying the first in-focus evaluation value by a given coefficient that is smaller than 1 to calculate the threshold value when the first in-focus evaluation value is larger than the second in-focus evaluation value, and multiplying the second in-focus evaluation value by the given coefficient to calculate the threshold value when the second in-focus evaluation value is larger than the first in-focus evaluation value.

5. The endoscope system as defined in claim 3, further comprising a memory that stores characteristic information about the first in-focus evaluation value and characteristic information about the second in-focus evaluation value when a distance to an object is changed in a form of a table,
    wherein the target in-focus position determination section calculating a ratio of the first in-focus evaluation value and the second in-focus evaluation value, searching the table based on the ratio to estimate the in-focus evaluation value when the first in-focus evaluation value is equal to the second in-focus evaluation value, and multiplying the estimated in-focus evaluation value by a given coefficient to calculate the threshold value.

6. The endoscope system as defined in claim 1, wherein the change-in-scene detection section detecting whether or not the change in scene has occurred by comparing image signals of a first captured image among a plurality of captured images sequentially acquired by the imaging section with image signals of a second captured image acquired prior to the first captured image.

7. The endoscope system as defined in claim 6, wherein the change-in-scene detection section calculating an amount of change between the image signals of the first captured image and the image signals of the second captured image, and determining that the change in scene has occurred when the amount of change is larger than a threshold value.

8. The endoscope system as defined in claim 6, wherein the change-in-scene detection section detecting whether or not the change in scene has occurred based on a result of motion detection between the first captured image and the second captured image.

9. The endoscope system as defined in claim 1, wherein the controller further comprising a control section that changes an imaging condition for the captured image,
wherein the change-in-scene detection section determining that the change in scene has occurred when the change-in-scene detection section has detected that the imaging condition have been changed by the control section.

10. The endoscope system as defined in claim 9, wherein the control section changing the imaging condition for the captured image based on operation information from a user that has been received by an operation section.

11. The endoscope system as defined in claim 9, wherein the control section setting an observation mode as the imaging condition, and
the change-in-scene detection section determining that the change in scene has occurred when the change-in-scene detection section has detected that the observation mode has been changed by the control section.

12. The endoscope system as defined in claim 11, wherein the observation mode including a normal light observation mode in which a normal light image is captured, and a special light observation mode in which a special light image is captured, the normal light image being an image that includes information within a wavelength band of white light, and the special light image being an image that includes information within a specific wavelength band.

13. The endoscope system as defined in claim 12, wherein the specific wavelength band being a band that is narrower than the wavelength band of the white light.

14. The endoscope system as defined in claim 13, wherein the normal light image and the special light image being in vivo images, and the specific wavelength band included in the in vivo images being a wavelength band of light absorbed by hemoglobin in blood.

15. The endoscope system as defined in claim 14, wherein the specific wavelength band being 390 to 445 nm or 530 to 550 nm.

16. The endoscope system as defined in claim 9, wherein the controller further comprising an image processing section that performs a contrast enhancement process on the captured image,
wherein the control section setting a degree of enhancement used for the contrast enhancement process as the imaging condition, and
the change-in-scene detection section determining that the change in scene has occurred when the change-in-scene detection section has detected that the degree of enhancement used for the contrast enhancement process has been changed by the control section.

17. The endoscope system as defined in claim 9, wherein the controller further comprising an image processing section that performs a noise reduction process on the captured image,
wherein the control section setting a degree of reduction used for the noise reduction process as the imaging condition, and
the change-in-scene detection section determining that the change in scene has occurred when the change-in-scene detection section has detected that the degree of reduction used for the noise reduction process has been changed by the control section.

18. The endoscope system as defined in claim 9, wherein the determination criterion being a condition whereby the in-focus evaluation value is larger than a threshold value, and
the target in-focus position determination section multiplying a current threshold value by a given coefficient that corresponds to details of a change in the imaging condition to calculate a new threshold value when the change-in-scene detection section has detected a change in the imaging condition as the change in scene, and using the new threshold value as the threshold value.

19. The endoscope system as defined in claim 18, wherein the target in-focus position determination section maintaining the first in-focus object plane position or the second in-focus object plane position that is selected as the in-focus object plane position of the imaging section as the target in-focus position when the change-in-scene detection section has detected a change in the imaging condition as the change in scene, and setting the first in-focus object plane position or the second in-focus object plane position that is not selected as the in-focus object plane position of the imaging section to be the target in-focus position when the target in-focus position determination section has determined that the in-focus evaluation value is smaller than the threshold value updated with the new threshold value.

20. A focus control method for an endoscope system comprising:
calculating an in-focus evaluation value based on a captured image acquired by an imaging section;
detecting whether or not a change in scene has occurred based on the captured image;
determining whether or not the in-focus evaluation value satisfies a determination criterion until it is detected that the change in scene has occurred;
determining a first in-focus object plane position or a second in-focus object plane position that is not currently selected to be a target in-focus position when it has been determined that the in-focus evaluation value does not satisfy the determination criterion, the first in-focus object plane position or the second in-focus object plane position being set to an in-focus object plane position of the imaging section;
switching the in-focus object plane position of the imaging section to the target in-focus position; and
updating the determination criterion when it is detected that the change in scene has occurred.

* * * * *